US011844864B2

(12) United States Patent
Krumme et al.

(10) Patent No.: US 11,844,864 B2
(45) Date of Patent: Dec. 19, 2023

(54) METHOD FOR PREPARING GRANULES

(71) Applicant: NOVARTIS AG, Basel (CH)

(72) Inventors: Markus Krumme, Allschwil (CH); Hans De Waard, Basel (CH); Klaus-Peter Moll, Basel (CH); Adrian Schmidt, Weil am Rhein (DE); Julien Taillemite, Huningue (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/640,789

(22) PCT Filed: Aug. 30, 2018

(86) PCT No.: PCT/IB2018/056629
§ 371 (c)(1),
(2) Date: Feb. 21, 2020

(87) PCT Pub. No.: WO2019/043614
PCT Pub. Date: Mar. 7, 2019

(65) Prior Publication Data
US 2021/0069114 A1    Mar. 11, 2021

(30) Foreign Application Priority Data
Aug. 31, 2017  (EP) .................... 17188800

(51) Int. Cl.
*A61K 9/16* (2006.01)
*A61K 9/00* (2006.01)
*A61K 9/20* (2006.01)
*A61K 9/48* (2006.01)
*A61K 31/192* (2006.01)

(52) U.S. Cl.
CPC .......... *A61K 9/1694* (2013.01); *A61K 9/0053* (2013.01); *A61K 9/1611* (2013.01); *A61K 9/1617* (2013.01); *A61K 9/1635* (2013.01); *A61K 9/1652* (2013.01); *A61K 9/2009* (2013.01); *A61K 9/2013* (2013.01); *A61K 9/2027* (2013.01); *A61K 9/2054* (2013.01); *A61K 9/2095* (2013.01); *A61K 9/485* (2013.01); *A61K 9/4833* (2013.01); *A61K 9/4858* (2013.01); *A61K 9/4866* (2013.01); *A61K 31/192* (2013.01)

(58) Field of Classification Search
CPC .. A61K 9/1694; A61K 9/0053; A61K 9/1611; A61K 9/1617; A61K 9/1635; A61K 9/1652; A61K 9/2009; A61K 9/2013; A61K 9/2027; A61K 9/2054; A61K 9/2095; A61K 9/4833; A61K 9/485; A61K 9/4858; A61K 9/4866; A61K 31/192

See application file for complete search history.

(56) References Cited

U.S. PATENT DOCUMENTS

| | | | | |
|---|---|---|---|---|
| 8,242,070 B2 * | 8/2012 | Fujioka | ................... | C11D 11/00 510/495 |
| 8,708,551 B2 * | 4/2014 | Hansen | ...................... | B01J 2/10 366/301 |
| 10,231,932 B2 * | 3/2019 | Swinney | ............... | A61K 9/1694 |
| 2003/0090039 A1 * | 5/2003 | Ghebre-Sellassie | ........................ | A61K 9/2009 264/117 |
| 2016/0250213 A1 * | 9/2016 | Simone | ................ | A61K 31/506 514/255.06 |
| 2016/0354316 A1 * | 12/2016 | Swinney | .................. | A61P 43/00 |
| 2017/0319486 A1 * | 11/2017 | Upadhye | ............... | A61K 9/1694 |
| 2019/0263042 A1 * | 8/2019 | Bhushan | ................. | B29B 7/483 |
| 2019/0263043 A1 * | 8/2019 | Bhushan | ................. | B29B 7/481 |

FOREIGN PATENT DOCUMENTS

| | | |
|---|---|---|
| EP | 2368543 A1 | 9/2011 |
| GB | 2540400 A | 1/2017 |
| WO | 2001/89679 A2 | 11/2001 |
| WO | WO 2014/093073 | 6/2014 |

OTHER PUBLICATIONS

Vercruysse et al. Continuous twin screw granulation: Influence of process variables on granule and tablet quality. European Journal of Pharmaceutics and Biopharmaceutics 82 (2012) 205-211. (Year: 2012).*

Vercruysse, J. et al: "Stability and repeatability of a continuous twin screw granulation and drying system", European Journal of Pharmaceutics and Biopharmaceutics, vol. 85, No. 3, May 21, 2013, pp. 1031-1038.

Seem Tim Chan et al: "Twin screw granulation—A literature re", Powder Technology, vol. 276, Feb. 7, 2015, pp. 89-102.

* cited by examiner

*Primary Examiner* — Robert A Wax
*Assistant Examiner* — Olga V. Tcherkasskaya
(74) *Attorney, Agent, or Firm* — Daniel E. Raymond

(57) ABSTRACT

A method for preparing granules. A slurry containing solid API powder particles dispersed in a liquid is prepared. The slurry is fed to a granulator and mixed with a dry base powder within the granulator in order to produce a slurry/base powder mixture. The slurry/base powder mixture produced within the granulator is dried in order to obtain granules containing the solid API particles and the base powder.

15 Claims, 5 Drawing Sheets

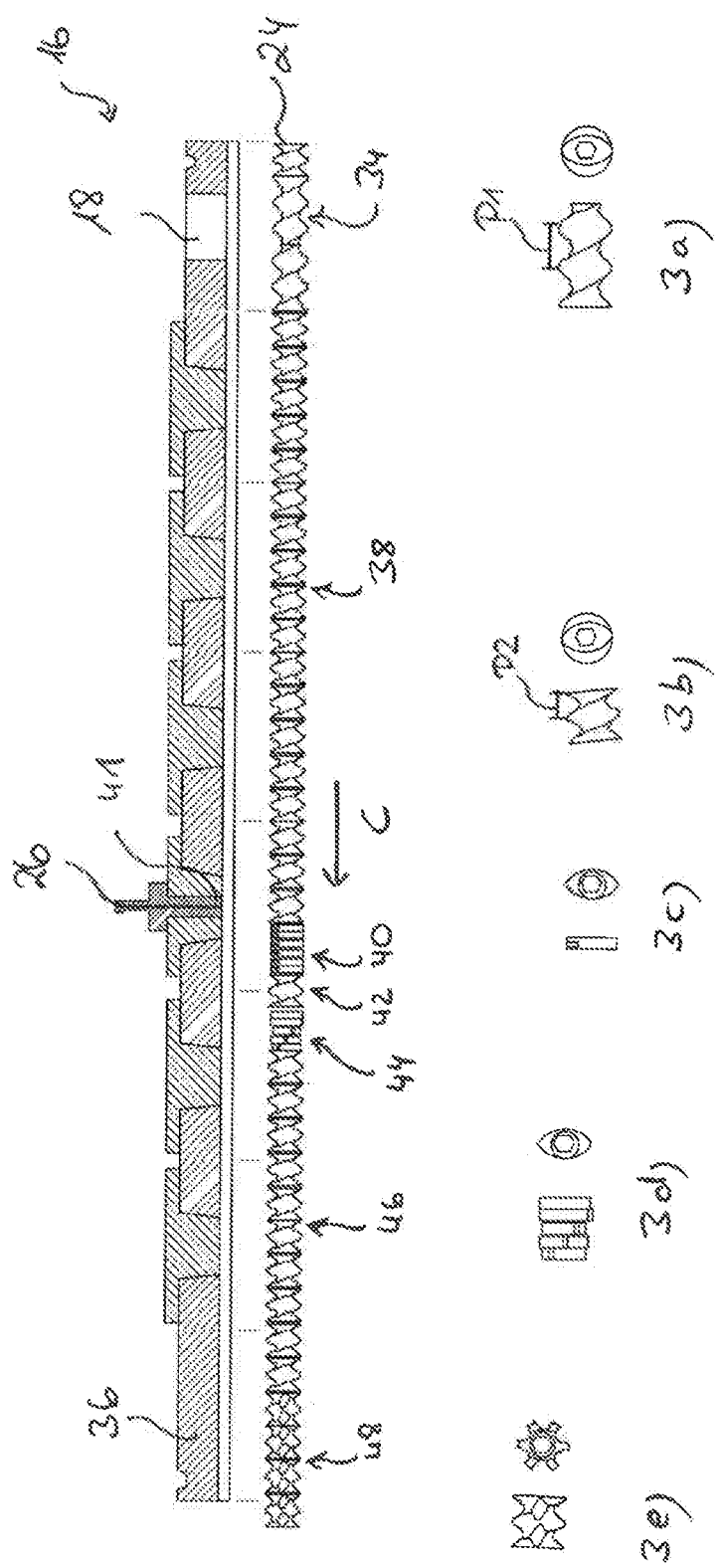

METHOD FOR PREPARING GRANULES

Figure 1:
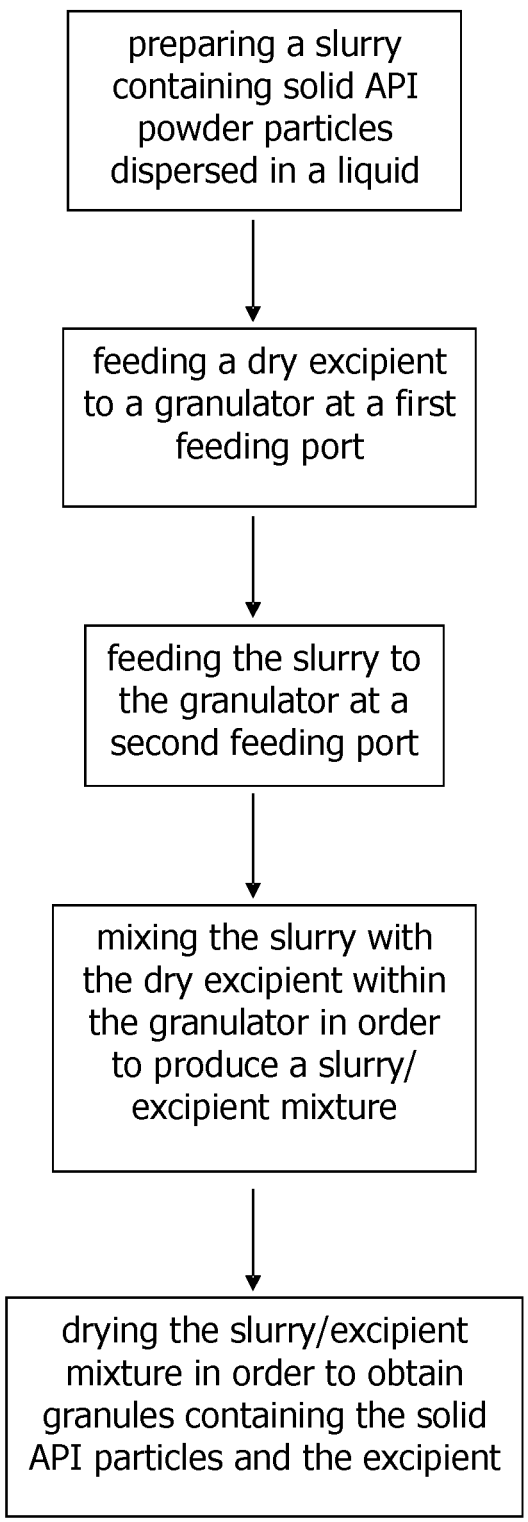

The invention relates to a method for preparing granules. Further, the invention relates to a method for manufacturing solid oral dosage forms containing granules of this kind.

Active pharmaceutical ingredients (API) intended for oral dosage typically undergo a number of synthesizing and washing steps in a liquid and finally are dried, for example by evaporation separation, in order to isolate the pure API from the auxiliary liquid phase used during the crystallization and washing steps. Thereafter, the primary API powder particles are further processed in order to form granules, i.e. multi-particulate entities suitable either for direct oral dosage or for further processing in order to prepare oral dosage forms such as tablets or capsules. Wet granulation of the dried pure API is a widely applied process step to enlarge particle sizes, to transform the properties of the API to enhance flow, compressibility, dissolution and hence biological exposure of the formulated compound and/or to dilute the concentration of the pure API to enable a volumetric dosing of the API during later processing steps.

For example, the dried pure API may be mixed with a binder and/or a granulation liquid such as water or an aqueous binder solution and thereafter again dried. In particular high-shear mixers with subsequent fluid bed drying or fluid bed dryers with the granulation liquid being sprayed into a fluidized powder bed may be used for producing dry granules that consist of the primary API particles bound together by a binding agent. These dry granules may already be suitable for oral dosage or can be further processed into a desired solid oral dosage form. Alternatively, the API and suitable excipients may be fed as dry solid particles to a screw granulator. A granulation liquid may be added separately into the granulator and after extensive mixing and due to applied shear, wet granules are obtained. These wet granules are dried and thereafter again may already be suitable for oral dosage or can be further processed into a desired solid oral dosage form. In any case, the drug substance to be further processed in the granulation step is provided in the form of a dry solid powder which requires batch processing, for example upon gravimetric dosing of the powder to be mixed with a binder and/or further excipients in the granulation step.

The invention is directed at the object of providing a method which allows an efficient preparation of granules. Further, the invention is directed at the object of providing a method for manufacturing solid oral dosage forms containing granules of this kind.

This object is addressed by a method for preparing granules as defined in claim 1 and a method for manufacturing solid oral dosage forms as defined in claim 15.

In the method for preparing granules, a slurry is prepared which contains solid API powder particles that are dispersed in a liquid. The slurry is fed to a granulator. In dependence on the type of the API and the properties of the API powder such as, for example, particle size, particle size distribution, surface properties, wetting properties, etc., a concentration of the API within the suspension may be between 10 to 70 weight %. For example, when using ibuprofen as the API, the concentration of the API within the suspension may be between 29 to 53 weight %, when using lumefantrine as the API, the concentration of the API within the suspension may be between 25 to 35 weight %, and when using Opadry yellow as a model API, the concentration of the model API within the suspension may be between 10 to 20 weight %. In any case, the flow properties of the suspension should be adjusted by appropriately selecting the API load in the suspension and the type of liquid used for preparing the slurry in such a manner that the slurry can be reliably fed to the granulator in a desired volumetric amount and with a desired feed rate.

Within the granulator, the slurry is mixed with a dry base powder in order to produce a slurry/base powder mixture. Finally, the slurry/base powder mixture produced within the granulator is dried in order to obtain granules containing the solid API particles and the base powder. In the context of this application, the expression "dry base powder" should designate a solid material in powder form which does not contain more than 10% residual moisture. The liquid/solid ratio within the slurry/base powder mixture mainly depends on the API concentration and the targeted drug load in the final composition and may be between 0.4 to 2.0. For example, when using ibuprofen as the API, the liquid/solid ratio within the slurry/base powder mixture may be between 0.5 to 1.4, when using lumefantrine as the API, the liquid/solid ratio within the slurry/base powder mixture may approximately 0.6, and when using Opadry yellow as a model API, the liquid/solid ratio within the slurry/base powder mixture may be between 0.2 and 0.4. Basically, the solid content within the slurry/base powder mixture should be as high as possible in order to reduce the drying time of the slurry/base powder mixture. On the other hand, the liquid content within the slurry/base powder mixture should be high enough to allow the formation of granules and proper mixing of the solid API particles with the base powder so as to ensure homogeneous distribution of the API in the resulting granules.

In dependence on the type of API and the desired route of administration, the granules obtained by the method described herein may be intended for direct oral dosage or may be intended for further processing into a desired administration form. In particular, the granules are suitable for further processing into solid oral dosage forms, such as tablets or capsules. The dried granules do not contain more than 5% residual moisture. Typical dried granule sizes vary from 200 to 1000 µm. Further, the dried granules provide for the desired biological exposure of the API, i.e. the desired dissolution of the API in the body of a patient.

In the method for preparing granules, fine gravimetric dosing of dry API powder can be dispensed with. Instead, the API can be reliably fed to the granulator in a desired amount by simply adjusting the API content, i.e. the API concentration within the slurry and the feed rate of the slurry to the granulator. Hence, time-saving and cost efficient continuous volumetric dosing of the API powder is made possible. In addition, mixing the API with the base powder with the API particles being dispersed in a liquid, may reduce stress and shear applied to the API particles during mixing and hence may be beneficial for the quality of the API.

In a preferred embodiment of the method for preparing granules, the dry base powder and the slurry are fed to the granulator at separate feeding ports. For example, the dry base powder may be fed to the granulator at a first feeding port, whereas the slurry may be fed to the granulator at a second feeding port. Preferably, the second feeding port is arranged downstream of the first feeding port. This allows the dry base powder to be pre-processed in the granulator before the slurry is added. The pre-processing of the dry base powder may, for example, include pre-compressing of the dry base powder prior to the addition of the slurry. The second feeding port may comprise a feeding nozzle which allows the supply of the slurry to the granulator at a desired feed rate.

The feed rate of the dry base powder to the granulator and the feed rate of the slurry to the granulator may vary in dependence on the design and in particular the dimensions of the granulator, the flow properties of the dry base powder, the API load, i.e. the liquid/solid ratio within the slurry, the rheology, in particular the viscosity of the slurry, the liquid/solid ratio within the slurry/base powder mixture, the rheology, in particular the viscosity of the slurry/base powder mixture, the wetting behavior of the dry base powder with the liquid contained in the slurry, the solubility of the API and the base powder in the liquid contained in the slurry, the granulation behaviour of the solids, i.e. the required amount of liquid to form granules with favourable properties, etc. Typical feed rates of the dry base powder to a small scale granulator with a 11 mm diameter screw may, e.g., vary between 140 and 500 g/h, whereas typical slurry feed rates to the small scale granulator may vary between 200 and 1000 g/h. Typical feed rates to a medium scale granulator with a 16 mm diameter screw may be up to 10 times higher and typical feed rates to a large scale granulator with a 47 mm diameter screw may be up to 50 kg/h.

The granulator may be designed in the form of a continuous granulator. The use of a continuous granulator further enhances the efficiency of the granules preparation process. Preferably, the granulator is designed in the form of an extruder which allows reliable granulation of the slurry/base powder mixture. Particularly effective mixing of the dry base powder with the API containing slurry is made possible, if the extruder is designed in the form of a twin screw extruder, wherein the screws engage with each other and are therefore self-cleaning.

At least one extruder screw of the granulator may comprise a base powder supply zone for conveying the dry base powder into an extruder housing. The base powder supply zone of the extruder screw may have a first pitch. Preferably, the base powder supply zone of the extruder screw is substantially aligned with the first feeding port via which the dry base powder is fed to the granulator such that a suction force induced by the rotation of the extruder screw conveys the dry base powder into the granulator. Alternatively or additionally thereto, the extruder screw may comprise a first compression zone. Preferably, the first compression zone of the extruder screw is arranged downstream of the base powder supply zone and has a second pitch which is smaller than the first pitch. Upon being conveyed through the first compression zone, the dry base powder may be densified prior to the addition of the slurry. In the context of this application, the terms "downstream" and "upstream" refer to a conveying direction of the dry base powder and the slurry/base powder mixture, respectively, through the granulator.

The extruder screw may also comprise a first granulation zone for kneading the slurry with the dry base powder. The first granulation zone may be arranged downstream of the first compression zone. Further, the first granulation zone may be aligned with or be arranged immediately downstream of the second feeding port via which the slurry is fed to the granulator. In particular in case the slurry is supplied to the granulator via a feeding nozzle, an additional suction force for conveying the slurry into the granulator is not required and the extruder screw does not need to be provided with a slurry supply zone. Instead, the slurry can be fed to the granulator either in the region of a downstream end of the first compression zone or in the region of an upstream end of the first granulation zone.

The extruder screw may further be provided with a second compression zone. In the second compression zone, the slurry/base powder mixture may be conveyed and densified. The second compression zone of the extruder screw may be arranged downstream of the first granulation zone. In the second compression zone, the extruder screw may have a pitch that is equal to the second pitch of the extruder screw in the first compression zone. In dependence on the properties of the slurry/base powder mixture, in particular the liquid/solid ratio within the slurry/base powder mixture and the viscosity of the slurry/base powder mixture, the pitch of the extruder screw in the second compression zone may, however, also be suitably adapted so as to be larger or smaller than the second pitch.

Further, the extruder screw may comprise a second granulation zone for kneading the slurry with the dry base powder. The second granulation zone may be arranged downstream of the second compression zone. If desired, a third compression zone for further conveying and densifying the slurry/base powder mixture may be provided on the extruder screw. The third compression zone may be arranged downstream of the second granulation zone. In the third compression zone, the extruder screw may have a pitch that is equal to the second pitch of the extruder screw in the first compression zone. In dependence on the properties of the slurry/base powder mixture, in particular the liquid/solid ratio within the slurry/base powder mixture and the viscosity of the slurry/base powder mixture, the pitch of the extruder screw in the third compression zone may, however, also be suitably adapted so as to be larger or smaller than the second pitch. Further, the pitch of the extruder screw in the third compression zone may be equal to or different from the pitch of the extruder screw in the second compression zone.

Finally, the extruder screw may comprise a homogenization zone for homogenizing the slurry/base powder mixture. Preferably the homogenizing zone is arranged downstream of the third compression zone. In the homogenizing zone, the screw may, for example, be designed in the form of a distributive feed screw which provides for a final homogenization of the slurry/base powder mixture prior to exiting the granulator.

Basically, the liquid contained in the slurry may be any desired liquid which is added to a previously dried API powder. Preferably, however, the liquid contained in the slurry contains a synthesizing liquid used for synthesizing the solid API powder particles in a preceding API synthesizing step or a washing liquid used for washing the solid API powder particles in a preceding washing step. In case a liquid used in a preceding API synthesizing step or a preceding washing step is "reused" as a granulation liquid in the granules preparation process, drying of the API prior to granulation processing can be dispensed with. In other words, a step of drying the API powder after synthesizing and/or washing which is energy and time intensive and hence unattractive from a cost perspective is no longer necessary. Further, also additional corrective processing steps such as milling or sieving that might be required after drying of pure API powders in order to maintain the desired particle properties and/or to obtain an API powder with good flowability which is suitable for further processing may be omitted. Finally, exposing the pure API to the thermal stress of drying can be avoided. For example, a wet filter cake obtained by filtering an API containing washing liquid after the washing step may be used as the slurry or as a basis for the slurry which may be diluted with further (washing) liquid if needed. The wet filter cake may, e.g., contain approximately 50% of solid API powder particles.

The slurry may contain only solid API particles and a liquid phase consisting of a synthesizing liquid used for synthesizing the solid API powder particles in a preceding API synthesizing step and/or a washing liquid used for washing the solid API powder particles in a preceding washing step. It is, however, also conceivable to add further liquid or solid components to the slurry for tailoring slurry properties such as, for example, dispersion of the API particles in the liquid phase, wetting of the API particles by the liquid phase, viscosity of the slurry, etc. For example, polysorbate, sodium pyrophosphate or another surfactant may be added to the slurry as a wetting agent.

Preferably, the liquid contained in the slurry contains water and/or at least one organic solvent, in particular ethanol, methanol, isopropanol and ethylacetate. Water and organic solvents, in particular ethanol, are suitable as dual-purpose liquids, i.e. liquids which are suitable for use as a washing agent upon washing pure API, for example after crystallization, and also for use as a granulation liquid.

In a preferred embodiment of the method for preparing granules, the dry base powder contains a binder. The addition of a binder allows the formation of granules, i.e. powder agglomerates from primary API particles.

Basically, the dry base powder may be an excipient and may consist exclusively of a single binder or a binder mixture. It is, however, also conceivable that the dry base powder contains further additives for tailoring the properties of the slurry/base powder mixture and/or the resulting granules as desired. For example, the dry base powder may be a binder containing pre-blend, i.e. a base powder mixture which is prepared, i.e. mixed or blended prior to being supplied to the granulator.

The dry base powder may, however, also contain or consist of solid API powder particles. In particular, the dry base powder may contain powder particles of the same API that is also contained in the slurry fed to the granulator. As a result, more or less pure API granules may be obtained. API granules prepared by granulating an API containing slurry with an API containing base powder may be partially recirculated to the granulator and re-used as dry base powder to be mixed with API containing slurry. For example, 50% of the granules prepared by granulating an API containing slurry with an API containing base powder may be continuously recirculated to the granulator in order to serve as dry base powder to be mixed with further API containing slurry.

In particular, the dry base powder may contain at least one of lactose, cellulose, in particular microcrystalline cellulose, sodium carboxymethyl cellulose, glyceryl behenate, magnesium stearate, sodium stearyl fumarate, polyvinylpyrrolidone, and calcium phosphate.

In a preferred embodiment of the method for preparing granules, the slurry is fed to the granulator by means of a metered pump. By using a metered pump, a reliable continuous volumetric dosing of the slurry to the granulator is made possible.

The dry base powder may be fed to the granulator by means of a powder dosing device which is controlled in dependence on a weight change of a reserve of the dry base powder contained in a reservoir of the powder dosing device. As compared to pure dry API powders, which, due to the small powder amounts to be dosed, require discontinuous fine gravimetric dosing, the dry base powder may be dosed to the granulator by means of weight change controlled powder dosing device with the required accuracy. Thus, also a continuous supply of the dry base powder to the granulator may be achieved, at least as long as a sufficient amount of dry base powder is present in the reservoir of the powder dosing device.

The granulation process may be interrupted for refilling the reservoir of the powder dosing device with the base powder. It is, however, also conceivable to simply interrupt the weight change control and to maintain the feed rate of base powder to the granulator constant, i.e. to operate the powder dosing device "blind" during refilling the reservoir.

The API contained within the slurry may contain at least one of ibuprofen, lumefantrine, and LDK378.

The slurry/base powder mixture exiting the granulator may be dried by means of a continuous or semi-continuous dryer. In particular, a fluid bed dryer may be used for drying the slurry/base powder mixture exiting the granulator. Fluid bed dryers are already commonly used in the pharmaceutical industry for drying both pure API powders and granules such that well-established drying process parameters can be relied upon in the method for preparing granules.

In a preferred embodiment of the method for preparing granules, a drying temperature for drying the slurry/base powder mixture is higher than the evaporation temperature of the liquid contained in the slurry. For example, the drying temperature for drying the slurry/base powder mixture may be between 50 and 75° C., in particular between 60 and 70° C. As a result, the thermal stress applied on the API during the drying step is limited. A drying time for removing 95% of the liquid contained in the granules exiting the granulator preferably does not exceed 35 minutes, in particular does not exceed 20 minutes, and preferably does not exceed 12 minutes. Limitation of the drying time enhances the overall efficiency of the granules preparation process.

In a method for manufacturing solid oral dosage forms granules are prepared in accordance with an above described method. The obtained granules are compacted so as to form tablets. Alternatively, the obtained granules are filled into capsules.

Figure 2:
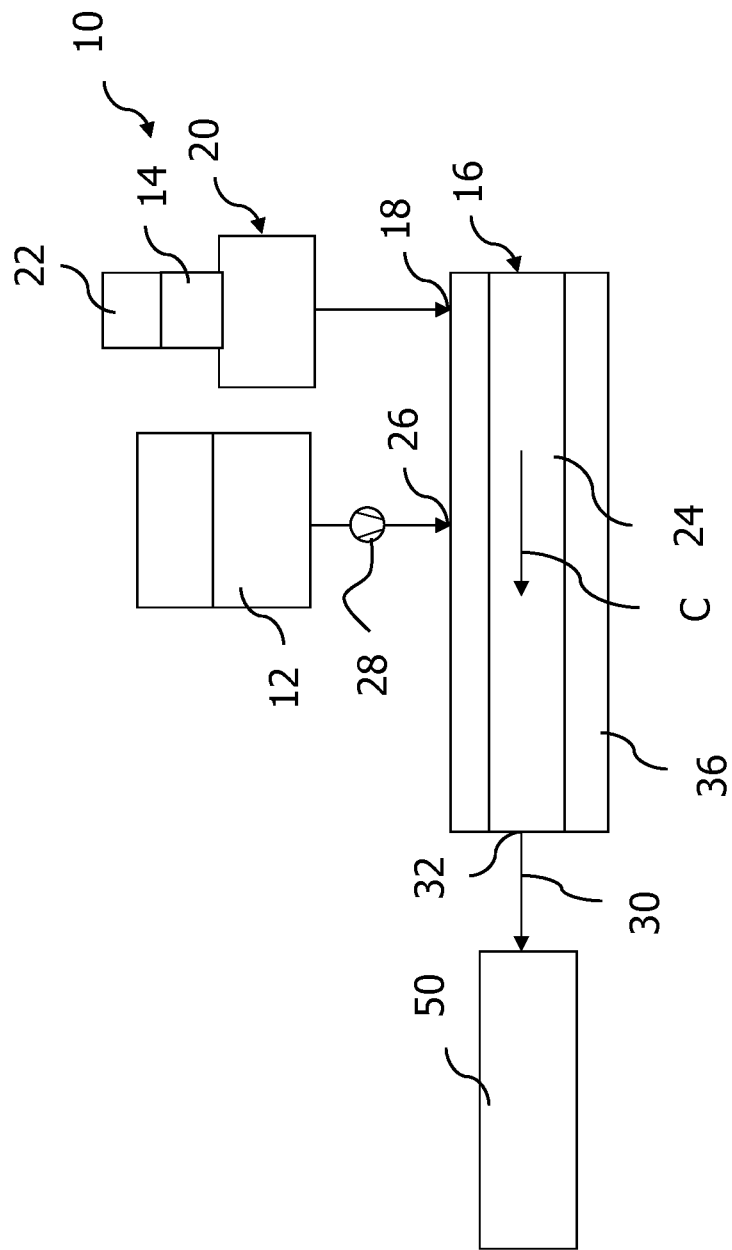
Figure 4A:
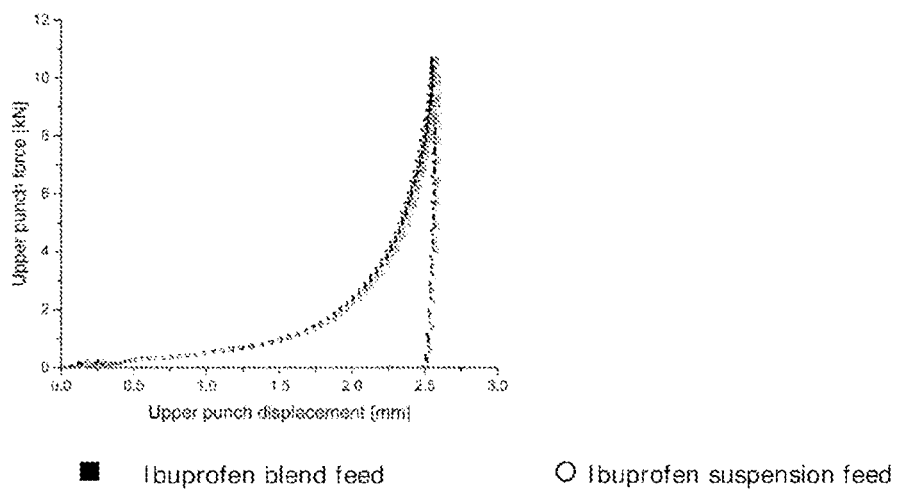
Figure 4B:
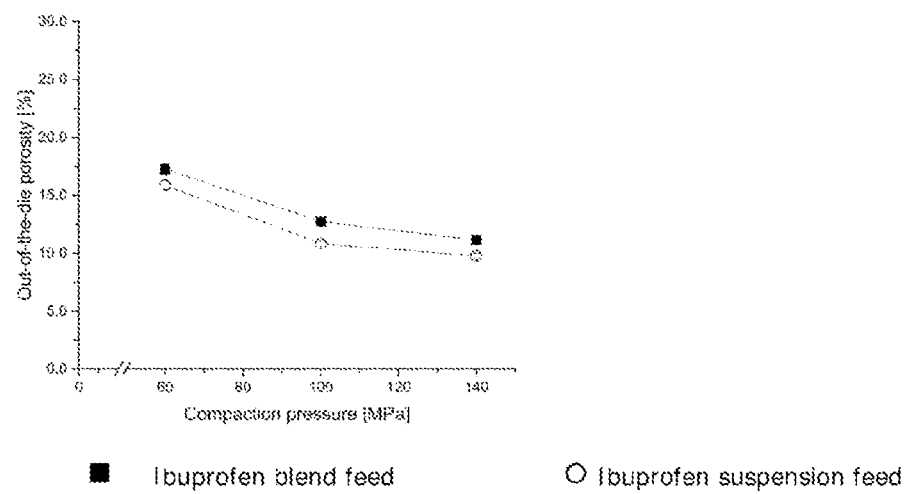
Figure 5:
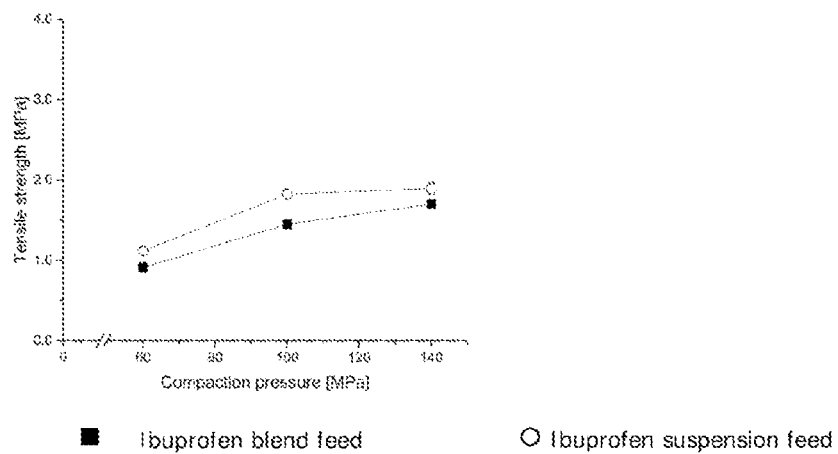
Figure 6:
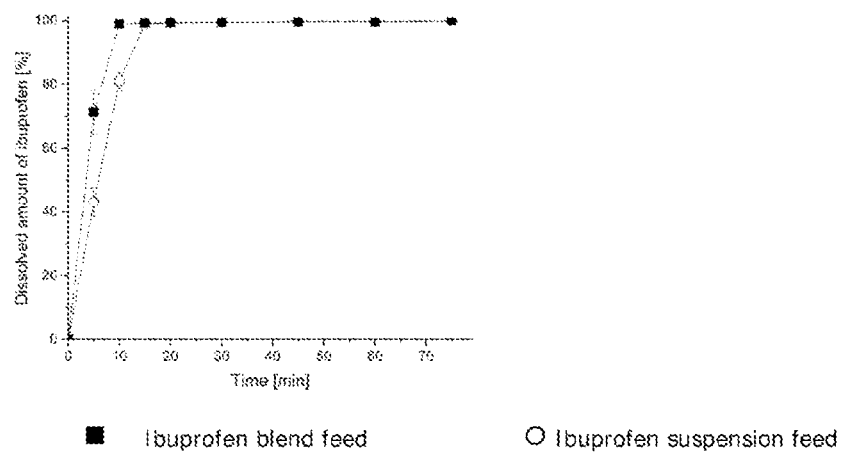

Preferred embodiments of the invention now will be described in greater detail with reference to the appended schematic drawings and examples, wherein:

FIG. 1 shows a flow diagram depicting a method for preparing granules,

FIG. 2 shows a layout of a system for preparing granules in accordance with the method of FIG. 1, FIG. 3 shows a detailed view of a granulator used in the system for preparing granules in accordance with FIG. 2, FIG. 4a shows a graph which is representative for the compaction behaviour of granules prepared in accordance with the method of FIG. 1 as compared to conventionally prepared granules, FIG. 4b shows a further graph which is representative for the compaction behaviour of granules prepared in accordance with the method of FIG. 1 as compared to conventionally prepared granules, FIG. 5 shows a graph which is representative for the mechanical properties of compacts produced from granules prepared in accordance with the method of FIG. 1 as compared to compacts produced from conventionally prepared granules, and FIG. 6 shows a graph which is representative for the dissolution behaviour of compacts produced from granules prepared in accordance with the method of FIG. 1 as compared to compacts produced from conventionally prepared granules.

FIG. 1 shows a flow diagram illustrating the main steps of a method for preparing granules. A layout of a system 10 for preparing granules in accordance with the method depicted in FIG. 1 is shown in FIG. 2. The method for preparing granules comprises a step of preparing a slurry 12 containing solid API powder particles which are dispersed in a liquid.

Basically, the slurry 12 may be prepared by adding a previously dried API powder to a liquid. In the preferred embodiment of the method depicted in FIG. 1, the liquid contained in the slurry 12, however, is a washing liquid used for washing solid API powder particles after being synthesized in a liquid phase in a preceding washing step. Hence, the solid API powder particles, after being washed, remain dispersed in the washing liquid. For example, a wet filter cake obtained by filtering an API containing washing liquid after the washing step may be used as the slurry or as a basis for the slurry which may be diluted with further (washing) liquid if needed. The washing liquid contained in the slurry 12 contains water and/or an organic solvent, in particular ethanol. If need be, liquid or solid additives for tailoring slurry properties such as, for example, dispersion of the API particles in the liquid phase, wetting of the API particles by the liquid phase, viscosity of the slurry, etc. may be added to the slurry 12.

Furthermore, a dry base powder 14 is provided. The base powder 14 contains a binder for powder agglomaration, for example polyvinylpyrrolidone. A selected binder may constitute the only component of the base powder 14. It is, however, also conceivable that the base powder 14 is a binder mixture or a binder containing powder pre-blend, i.e. a binder mixture or a binder containing powder mixture which is prepared in a preceding mixing step. Lactose and/or cellulose, in particular microcrystalline cellulose, may be added so as to serve as tablet binders/diluents. Glyceryl behenate, magnesium stearate, and/or sodium stearyl fumarate may be added as lubricants. Sodium carboxymethyl cellulose may be added as a disintegrant. Further, the dry base powder may contain or consist of solid API powder particles. In particular, the dry base powder may contain powder particles of the same API that is also contained in the slurry fed to the granulator.

As becomes apparent from FIG. 2, the dry base powder 14 is fed to a granulator 16 at a first feeding port 18 of the granulator 16. In particular, the dry base powder 14 is continuously fed to the granulator 16 by means of a powder dosing device 20 which is controlled in dependence on a weight change of a reserve of the dry base powder 14 contained in a reservoir 22 of the powder dosing device 20. Basically, it is conceivable to interrupt the supply of dry base powder 14 for refilling the reservoir 22 of the powder dosing 20 device with the base powder 14. In order to maintain a continuous supply of base powder 14 to the granulator 16, it is, however, preferable to simply interrupt the weight change control and to maintain the volumetric feed rate of base powder 14 to the granulator 16 constant, i.e. to operate the powder dosing device 20 "blind" during refilling the reservoir.

In the arrangement depicted in FIG. 2, the granulator 16 is designed in the form of a twin screw extruder, i.e. in the form of a continuous operable extruder device which is equipped with a pair of intermeshing extruder screws 24. The pair of extruder screws 24 is operable to rotate about respective central axes in order to convey an extrudate through the granulator 16 in a conveying direction which in FIG. 2 is indicated by the arrow C.

The slurry 12 is fed to the granulator 16 at a second feeding port 26 which, with respect to the conveying direction C, is arranged downstream of the first feeding port 18. In particular, the slurry 12 is fed to the granulator 16 by means of a metered pump 28. In dependence on the type of the API and the properties of the API powder such as, for example, particle size, particle size distribution, surface properties, wetting properties, etc., a concentration of the API within the suspension may be between 10 to 70 weight %. For example, when using ibuprofen as the API, the concentration of the API within the suspension may be between 29 to 53 weight %, when using lumefantrine as the API, the concentration of the API within the suspension may be between 25 to 35 weight %, and when using Opadry yellow as a model API, the concentration of the model API within the suspension may be between 10 to 20 weight %. In any case, in order to ensure a reliable continuous volumetric dosing of the slurry 12 to the granulator 16, the concentration of the API within the suspension, i.e. a liquid/solid ratio within the slurry 12 and a viscosity of the slurry 12 should be appropriately adjusted, if needed by means of the addition of solid or liquid additives to the slurry 12, in order to allow an unhindered pumping of the slurry 12 into the granulator 16.

A feed rate of the dry base powder 14 to the granulator 16 may vary in dependence on the flow properties of the powdery dry base powder 14, the API load of the slurry 12, i.e. the liquid/solid ratio within the slurry 12, the viscosity of the slurry 12, the liquid/solid ratio within a slurry/base powder mixture 30, the viscosity of the slurry/base powder mixture 30, the wetting behavior of the dry base powder 14 with the liquid contained in the slurry 12, etc. Typical feed rates of the dry base powder 14 to a small scale granulator 16 may vary between 140 and 500 g/h, whereas typical slurry feed rates to the small scale granulator 16 may vary between 200 and 1000 g/h. Typical feed rates to a medium scale granulator with a 16 mm diameter screw may be up to 10 times higher and typical feed rates to a large scale granulator with a 47 mm diameter screw may be up to 50 kg/h.

Within the granulator 16, the slurry 12 is mixed with the dry base powder 14 in order to produce a slurry/base powder mixture 30 exiting the granulator 16 at an outlet port 32. A detailed view of the granulator 16 is depicted in FIG. 3. As becomes apparent from FIG. 3, the extruder screws 24 of the granulator 16 comprise an base powder supply zone 34 for conveying the dry base powder into an extruder housing 36. The base powder supply zone 34 of the extruder screws 24 is substantially aligned with the first feeding port 18 via which the dry base powder 14 is fed to the granulator 16. In the base powder supply zone 34, each of the pair of extruder screws 24 has a first pitch P1 which allows the generation of a suction force by the rotation of the extruder screws 24 so as to convey the dry base powder 14 into the extruder housing 36. A detailed view, i.e. a detailed side view and a cross-sectional view, of the design of the extruder screws 24 in the base powder supply zone 34 is depicted in FIG. 3*a*.

Further, the extruder screws 24 comprise a first compression zone 38 for conveying and densifying the dry base powder supplied into the extruder housing 36 via the first feeding port 18. The first compression zone 38 of the extruder screws 24 is arranged downstream of the base powder supply zone 34, ends in a region of the second feeding port 26 and has a second pitch P2 which is smaller than the first pitch P1. A detailed view, i.e. a detailed side view and a cross-sectional view, of the design of the extruder screws 24 in the first compression zone 38 is depicted in FIG. 3*b*. Upon being conveyed through the first compression zone 38, the dry base powder is densified before the slurry is added via the second feeding port 26. The second feeding port 26 comprises a feeding nozzle 41 which allows the supply of the slurry to the granulator 16 at the desired feed rate.

Downstream of the first compression zone 38 and more or less immediately downstream of the second feeding port 26 the extruder screws 24 comprise a first granulation zone 40 for kneading the slurry with the dry base powder. A detailed view, i.e. a detailed side view and a cross-sectional view, of the design of the extruder screws 24 in the first granulation zone 40 is depicted in FIG. 3c.

In addition, the extruder screws 24, downstream of the first granulation zone 40, are provided with a second compression zone 42 wherein the extruder screws 24, in the exemplary embodiment of a granulator 16 shown in the drawings, have a pitch that is equal to the second pitch P2 of the extruder screws 24 in the first compression zone 38 and the design of the extruder screws 24 corresponds to the design of the extruder screws 24 in the first compression zone 38 as depicted in FIG. 3b. In the second compression zone 42, the slurry is further conveyed and densified. The pitch and the further design of the extruder screws 24 in the second compression zone 42 may, however, be adjusted as needed in dependence on the properties of the slurry/base powder mixture, in particular the liquid/solid ratio within the slurry/base powder mixture and the viscosity of the slurry/base powder mixture.

Further, the extruder screws 24 comprise a second granulation zone 44 for further kneading the slurry with the dry base powder. The second granulation zone 44 is arranged downstream of the second compression zone 42. A detailed view, i.e. a detailed side view and a cross-sectional view, of the design of the extruder screws 24 in the second granulation zone 44 is depicted in FIG. 3d.

A third compression zone 46 for further conveying and densifying the slurry/base powder mixture is provided on the extruder screws 24 downstream of the second granulation zone 44. In the third compression zone 46, the extruder screws 24 have a pitch that is equal to the second pitch P2 of the extruder screws 24 in the first compression zone 38 and the design of the extruder screws 24 corresponds to the design of the extruder screws 24 in the first compression zone 38 as depicted in FIG. 3b. Like the pitch and the design of the extruder screws 24 in the second compression zone 42, also the pitch and the further design of the extruder screws 24 in the third compression zone 46 may be adjusted as needed in dependence on the properties of the slurry/base powder mixture, in particular the liquid/solid ratio within the slurry/base powder mixture and the viscosity of the slurry/base powder mixture.

Finally, although the slurry/base powder mixture should already be homogenized upon exiting the second granulation zone 44, the extruder screws 24 are provided with a homogenization zone 48 for further homogenizing the slurry/base powder mixture. In particular, the homogenizing zone 48 is arranged downstream of the third compression zone 46 and the extruder screws 24, in the homogenizing zone 48, are designed in the form of a distributive feed screw which provides for a final homogenization of the slurry/base powder mixture prior to exiting the granulator 16. A detailed view, i.e. a detailed side view and a cross-sectional view, of the design of the extruder screws 24 in the homogenization zone 48 is depicted in FIG. 3e.

It should be acknowledged, that the dimensions, i.e. the lengths of the different zones 34, 38, 40, 42, 44, 46, 48 of the extruder screws 24 as well as the design of the different zones 34, 38, 40, 42, 44, 46, 48 of the extruder screws 24 may be varied as needed in dependence on the properties of the dry base powder, the slurry and the slurry/base powder mixture. Further, the extruder screws 24 may be cooled, at least in the region of the first and the second granulation zone 40, 44, e.g. by means of cooling channels provided in a housing of the granulator 16.

The slurry/base powder mixture exiting the granulator 16 via the outlet port 32 is dried by means of a continuous or semi-continuous dryer 50. In particular, the dryer 15 is designed in the form of a fluid bed dryer. A drying temperature for drying the slurry/base powder mixture is higher than the evaporation temperature of the liquid contained in the slurry and may be between 50 and 75° C., in particular between 60 and 70° C. A drying time for removing 95% of the liquid contained in the granules exiting the granulator 16 does not exceed 35 minutes, in particular does not exceed 20 minutes, and preferably does not exceed 12 minutes. Typical dried granule sizes vary from 200 to 1000 μm.

The granules obtained via the above-described method may be suitable for direct oral dosage or may be intended to be filled into capsules. Preferably, however, the granules are compacted so as to form tablets.

EXAMPLE 1

A granulation process with the colorant "Opadry Basic Lack Yellow" as surrogate for a drug substance was performed using the process parameters summarized in table 1.

TABLE 1

Example 1: a colorant as surrogate for a drug substance

| Solid feed composition | | Slurry feed composition | |
| --- | --- | --- | --- |
| Material | Concentration (% w/w) | Material | Concentration (% w/w) |
| Lactose milled | 60 | Opadry Basic Lack Gelb | 20 |
| Cellulose MK GR | 30 | Water | 80 |
| Glyceryl behenate | 10 | | |

| Equipment setup | |
| --- | --- |
| Twin screw granulator type: | Thermo Fisher 16 MM Pharma |
| Screw speed: | 200 rpm |
| Solid feed rate: | 1.00 kg/h |
| Slurry feed rate: | 0.25 kg/h |
| Temperature | 13-15° C. in all zones |

For the preparation of a slurry containing the colorant, the suspending agent water was mixed with the colorant until the desired concentration indicated in table 1 was obtained. The slurry was constantly stirred for the preparation and thereafter for at least further 30 minutes using an overhead stirrer equipped with a four-blade agitator in order to maintain a uniform solution/suspension.

Twin-screw wet granulation was performed on a co-rotating Pharma 16 mm twin-screw granulator (Thermo Scientific Pharma 16, Thermo Fisher Scientific, Karlsruhe, Germany). The twin-screw granulator was operated at a constant screw speed of 200 rpm. The temperature was kept constant at 13-15° C. in all zones. Powder components were directly fed into the twin-screw granulator from a continuous blender. The granulation liquid was dosed to the twin-screw granulator using a peristaltic pump (NM003BY11S12B, Netzsch Group, Selb, Germany).

Satisfactory wet granules suitable for further processing by drying and compacting were obtained.

EXAMPLE 2

A granulation process with the API LDK378 was performed using the process parameters summarized in table 2.

TABLE 2

Example 2: LDK378

| Solid feed composition | | Slurry feed composition | |
|---|---|---|---|
| Material | Concentration (% w/w) | Material | Concentration (% w/w) |
| MCC PH101 | 47.5 | LDK378.DS | 50.0 |
| PVP K30 | 12.5 | Water | 30.0 |
| Natrium CMC XL | 10.0 | Ethanol | 20.0 |
| Sodium Stearyl Fumerate | 30.0 | | |

Equipment setup

| | |
|---|---|
| Twin screw granulator type: | Thermo Fisher 11 MM Pharma |
| Screw speed: | 250 rpm |
| Solid feed rate: | 0.2 kg/h |
| Slurry feed rate: | 0.6 kg/h |
| Temperature | 20° C. in all zones |

For the preparation of a slurry containing the API, the API was dispensed in the suspending liquid until the desired concentration indicated in table 2 was obtained. No suspending agents were involved. The slurry was constantly stirred using an overhead stirrer equipped with a four-blade agitator in order to maintain a uniform solution/suspension.

Twin-screw wet granulation was performed on a co-rotating Pharma 11 mm twin-screw granulator (Thermo Scientific Pharma 11, Thermo Fisher Scientific, Karlsruhe, Germany). The twin-screw granulator was operated at a constant screw speed of 250 rpm. The temperature was kept constant at 20° C. in all zones. Powder components were fed into the twin-screw granulator using a Brabender gravimetric feeder (DDW-MDO-MT-1, Brabender, Duisburg, Germany). The feeder mass flow rate was calibrated via the internal calibration mode. The solid mass flow rate has then been verified by a dynamic balance (K-Sampler K-SFS-24, Coperion K-Tron, Pitman, USA), in order to exclude process fluctuations due to powder flow instabilities. The granulation liquid was dosed to the twin-screw granulator (using a progressing cavity pump (NM003BY11S12B, Netzsch Group, Selb, Germany).

Satisfactory wet granules suitable for further processing by drying and compacting were obtained.

EXAMPLES 3 to 5

Granulation processes with the API Ibuprofen were performed using varying process parameters as summarized in tables 3 to 5.

TABLE 3

Example 3: Ibuprofen (1)

| Solid feed composition | | Slurry feed composition | |
|---|---|---|---|
| Material | Concentration (% w/w) | Material | Concentration (% w/w) |
| MCC PH102 | 68.0 | Ibuprofen | 32.4-51.1 |
| PVP K30 | 6.7 | Polysorbate 80 | 0.2-0.3 |
| Natrium CMC XL | 21.4 | Water | 48.6-67.4 |
| Magnesium stearate | 4.0 | | |

TABLE 3-continued

Example 3: Ibuprofen (1)

Equipment setup

| | |
|---|---|
| Twin screw granulator type: | Thermo Fisher 11 MM Pharma |
| Screw speed: | 250 rpm |
| Solid feed rate: | 0.19 kg/h |
| Slurry feed rate: | 0.59-0.93 kg/h |
| Temperature | 20° C. in all zones |

TABLE 4

Example 4: Ibuprofen (2)

| Solid feed composition | | Slurry feed composition | |
|---|---|---|---|
| Material | Concentration (% w/w) | Material | Concentration (% w/w) |
| MCC PH102 | 72.8 | Ibuprofen | 43.8 |
| Natrium CMC XL | 22.9 | Sodium pyrophosphate | 1.8 |
| Magnesium stearate | 4.3 | PVP K30 | 1.8 |
| | | Water | 52.5 |

Equipment setup

| | |
|---|---|
| Twin screw granulator type: | Thermo Fisher 11 MM Pharma |
| Screw speed: | 250 rpm |
| Solid feed rate: | 0.18 kg/h |
| Slurry feed rate: | 0.69 kg/h |
| Temperature | 20° C. in all zones |

TABLE 5

Example 5: Ibuprofen (3)

| Solid feed composition | | Slurry feed composition | |
|---|---|---|---|
| Material | Concentration (% w/w) | Material | Concentration (% w/w) |
| MCC PH102 | 68.0 | Ibuprofen | 44.6-53.3 |
| PVP K30 | 6.7 | Sodium pyrophosphate | 1.9-2.2 |
| Natrium CMC XL | 21.3 | Water | 44.5-53.5 |
| Magnesium stearate | 4.0 | | |

Equipment setup

| | |
|---|---|
| Twin screw granulator type: | Thermo Fisher 11 MM Pharma |
| Screw speed: | 250 rpm |
| Solid feed rate: | 0.19 kg/h |
| Slurry feed rate: | 0.56-0.67 kg/h |
| Temperature | 20° C. in all zones |

For the preparation of a slurry containing the API, the suspending liquid (water) was pre-weighed. The suspending agent sodium pyrophosphate or polysorbate was dissolved in the suspending liquid. For example 5, PVP K30 was then dissolved in the liquid. After that, dry API powder was added in small portions until the desired concentration indicated in tables 3 to 5 was obtained. The slurry was constantly stirred using an overhead stirrer equipped with a four-blade agitator in order to maintain a uniform solution/suspension.

Twin-screw wet granulation was performed on a co-rotating Pharma 11 mm twin-screw granulator (Thermo Scientific Pharma 11, Thermo Fisher Scientific, Karlsruhe, Germany). The twin-screw granulator was operated at a constant screw speed of 250 rpm. The temperature was kept constant at 20° C. in all zones. Powder components were fed into the twin-screw granulator using a Brabender gravimetric feeder (DDW-MDO-MT-1, Brabender, Duisburg, Germany). The feeder mass flow rate was calibrated via the internal calibration mode. The solid mass flow rate has then been verified by a dynamic balance (K-Sampler K-SFS-24, Coperion K-Tron, Pitman, USA), in order to exclude process fluctuations due to powder flow instabilities. The granulation liquid was dosed to the twin-screw granulator (using a progressing cavity pump (NM003BY11S12B, Netzsch Group, Selb, Germany).

Drying of wet granules was performed using a fluid bed dryer (Mini Glatt 5, Glatt, Binzen, Germany). The cone of the fluid bed dryer was filled with the same volume of wet granules for each experiment, which corresponded to a wet mass of approximately 120 g. The airflow was increased until appropriate fluidisation of the granules was observed. The granules were dried at an inlet air temperature of 65° C.

COMPARATIVE EXAMPLE

Comparison was performed in detail for example 5. Traditional ibuprofen blend was fed to a co-rotating Pharma 11 mm twin-screw granulator (Thermo Scientific Pharma 11, Thermo Fisher Scientific, Karlsruhe, Germany). Therefore, all solid components were fed to the granulator as a dry powder blend. As granulation liquid, only water was added. The formulations of ibuprofen blend and ibuprofen suspension feed were quanitatively and qualitatively similar for L/S 0.5. The total solid mass flow rate (ibuprofen and excipients combined) was kept constant at 500 g/h, independent of whether the ibuprofen was dosed with the blend or as suspension (i.e. solids processed via the dry blend plus solids processed via the granulation liquid was equal to 500 g/h). The screw speed was 250 rpm, the temperature in all zones 20° C.

Drying of the granules was performed using a fluid bed dryer (Mini Glatt 5, Glatt, Binzen, Germany). The cone of the fluid bed dryer was filled with the same volume of wet granules for each experiment, which corresponded to a wet mass of approximately 120 g. The airflow was increased until appropriate fluidisation of the granules was observed. The granules were dried at an inlet air temperature of 65° C.

Characterization of the Granules

In order to study the impact of the adapted granulation process on the compaction behaviour of the granules and on compact properties, the granules obtained according to example 5 and the granules obtained according to the comparative example were compacted so as to form tablets and characterized as follows.

Prior compaction, granules were sieved through a 1 mm mesh. Round flat face compacts (11.28 mm diameter, compact mass 500 mg) were manufactured, using a fully instrumented compaction simulator equipped with a hopper (Stylcam® 200R, Medel-pharm, Beynost, France). A FETTE P1200 was mimicked. Varying compaction pressures (60 MPa, 100 MPa and 140 MPa) were applied with a dwell time of 13 ms.

Compacts were characterised by measuring compact height and diameter, out-of-the-die porosity, crushing force and dissolution time for ibuprofen. The compact height and diameter were assessed immediately after compaction, using callipers (Traceable®, VWR, Radnor, USA). The out-of-the-die porosity was calculated for 10 compacts produced at each compaction pressure by using the true density, the compact height and diameter, assessed immediately after compaction. The crushing force was measured (Pharmatron Multitest 50, Pharmatron, Thun, Switzerland) for 10 compacts produced at each compaction pressure. The dissolution time of compacts manufactured at 100 MPa was measured according to the USP for ibuprofen tablets (n=3). A paddle apparatus has been used (AT7 Smart double bath, Sotax, Aesch, Switzerland). After 60 min, the paddle speed was increased from 50 to 200 rpm and after 75 min, a final measurement cycle was performed. During a measurement cycle the media was pumped from the dissolution vessel to an in-line UV-spectrometer (Lambda 25, PerkinElmer instruments, Schwerzenbach, Switzerland) and back again to the vessel. UV-measurements were performed at a wavelength of 222 nm using a 1 mm measuring cell.

The compaction process of the dried granules from twin-screw wet granulation with API suspension feed has been compared to the compaction process of the dried granules from traditional API blend feed using force-displacement-curves. For dried granules of both processes, the force-displacement-curves from the compaction were almost overlaying, see FIG. 4a. This indicates that particle packing in the tablet die and compactability of the granules were comparable. The relative standard deviation in the mass of the compacts was found below 0.5%. As shown in FIG. 4b, the out-of-the-die porosity was observed to decrease with increasing compaction pressure (from 15.86% to 9.78% for the Ibuprofen slurry feed and from 17.28% to 11.15 for the Ibuprofen dry powder blend feed for 60 MPa, and 140 MPa compaction pressure, respectively). The out-of-the-die porosity was found to be slightly higher for the Ibuprofen powder blend feed in comparison to the Ibuprofen slurry feed for every applied compaction pressure.

This observation is in line with the trend found in the data of the tensile strength. The tensile strength has been observed consistently higher for the Ibuprofen slurry feed than for the Ibuprofen powder blend feed (1.1 versus 0.9 MPa, 1.8 versus 1.4 MPa, 1.9 versus 1.7 MPa, for 60, 100 and 140 MPa compaction pressure for Ibuprofen slurry feed versus Ibuprofen powder blend feed), see FIG. 5.

The dissolution rate for Ibuprofen compacts manufactured from the granules from the Ibuprofen slurry feed approach was slightly slower than for the compacts manufactured from granules from the Ibuprofen powder blend feed approach, see FIG. 6. This phenomenon could be assigned to the lower out-of-the-die porosity and the higher tensile strength of the compacts from the Ibuprofen slurry feed. In summary, for both twin-screw wet granulation approaches, the compacts were found to have comparable properties.

The invention claimed is:

1. A method for preparing granules, the method comprising:
   i. preparing a slurry containing solid active pharmaceutical ingredient (API) powder particles dispersed in a liquid,
   ii. feeding the slurry to a continuous granulator,
   iii. mixing the slurry with a dry base powder within the continuous granulator in order to produce a slurry/base powder mixture, wherein at least the mixing step is conducted at a temperature less than about 20° C.; and
   iv. drying the slurry/base powder mixture produced within the continuous granulator, wherein the slurry/base powder mixture exiting the continuous granulator is dried by means of a continuous or semi-continuous dryer, wherein a drying temperature for drying the slurry/base powder mixture is between 30 and 100° C., and wherein the resulting granules comprise the solid API particles and the base powder.

2. The method according to claim 1, wherein the dry base powder is fed to the continuous granulator at a first feeding port and the slurry is fed to the continuous granulator at a second feeding port which is arranged downstream of the first feeding port, the second feeding port comprising a feeding nozzle.

3. The method according to claim 1, wherein the continuous granulator has at least one extruder screw.

4. The method according to claim 3, wherein at least one extruder screw comprises at least one of:
- a base powder supply zone for conveying the dry base powder into an extruder housing, the base powder supply zone of the extruder screw having a first pitch;
- a first compression zone for conveying and densifying the dry base powder, the first compression zone being arranged downstream of the base powder supply zone and having a second pitch which is smaller than the first pitch;
- a first granulation zone for kneading the slurry with the dry base powder, the first granulation zone being arranged downstream of the first compression zone;
- a second compression zone for conveying and densifying the slurry/base powder mixture, the second compression zone being arranged downstream of the first granulation zone;
- a second granulation zone for kneading the slurry with the dry base powder, the second granulation zone being arranged downstream of the second compression zone;
- a third compression zone for conveying and densifying the slurry/base powder mixture, the third compression zone being arranged downstream of the second granulation zone, and
- a homogenization zone for homogenizing the slurry/base powder mixture, the homogenizing zone being arranged downstream of the third compression zone.

5. The method according to claim 1, wherein the liquid contained in the slurry contains a synthesizing liquid used for synthesizing the solid API powder particles in a preceding API synthesizing step or the liquid contained in the slurry contains
- a washing liquid used for washing the solid API powder particles in a preceding washing step.

6. The method according to claim 1, wherein the liquid contained in the slurry contains water and at least one organic solvent selected from ethanol, methanol, isopropanol and ethylacetate, or the liquid contained in the slurry contains water or at least one organic solvent selected from ethanol, methanol, isopropanol and ethylacetate.

7. The method according to claim 1, wherein the dry base powder contains a binder.

8. The method according to claim 7, wherein the dry base powder consists of a binder or wherein the dry base powder consists of a powder pre-blend containing a binder, and/or wherein the dry base powder contains solid API powder particles.

9. The method according to claim 1,
wherein the dry base powder comprises at least one of API, lactose, cellulose, microcrystalline cellulose, sodium carboxymethyl cellulose, glyceryl behenate, magnesium stearate, sodium stearyl fumarate, polyvinylpyrrolidone, and calcium phosphate.

10. The method according to claim 1,
wherein the slurry is fed to the continuous granulator by means of a metered pump.

11. The method according to claim 1, wherein the dry base powder is fed to the continuous granulator by means of a powder dosing device which is controlled in dependence on a weight change of a reserve of the dry base powder contained in a reservoir of the powder dosing device.

12. The method according to claim 1,
wherein the API contains at least one of ibuprofen, lumefantrine and LDK378.

13. A method for manufacturing solid oral dosage forms, wherein the method comprises:
   i. preparing granules in accordance with the method according to claim 1, and
   ii. compacting the granules so as to form tablets or filling the granules into capsules.

14. The method according to claim 1, wherein the liquid contained in the slurry comprises a synthesizing liquid used for synthesizing the solid API powder particles or a washing liquid used for washing the solid API powder particles.

15. The method according to claim 1, wherein a maximum temperature in any zone throughout the process is no greater than 75° C.

* * * * *